United States Patent [19]

Huse et al.

[11] Patent Number: 5,681,726
[45] Date of Patent: Oct. 28, 1997

[54] METHOD OF DOUBLE STRANDED DNA SYNTHESIS

[75] Inventors: William David Huse, Del Mar; Connie Jo Hansen, San Diego, both of Calif.

[73] Assignee: Stratagene, La Jolla, Calif.

[21] Appl. No.: 116,049

[22] Filed: Sep. 2, 1993

Related U.S. Application Data

[63] Continuation of Ser. No. 981,931, Nov. 23, 1992, abandoned, which is a continuation of Ser. No. 700,066, May 2, 1991, abandoned, which is a continuation of Ser. No. 246,567, Sep. 19, 1988, abandoned.

[51] Int. Cl.$^6$ ..................................................... C12P 19/34
[52] U.S. Cl. ..................................... 435/91.52; 435/172.1
[58] Field of Search ........................... 435/91.1, 91.5, 435/91.51, 91.33, 91.52, 172.1; 536/23.1, 25.3

[56] References Cited

PUBLICATIONS

Schreiber et al. "Selective Protection of in vitro Synthesized cDNA Against Nucleases by Incorporation of Phosphorothioate-Analogues" Nucleic Acids Research, vol. 13, No. 21, pp. 7663–7672, 1985.

Han et al. "Isolation of Full–Length Putative Rat Lysophospholipase cDNA Using Improved Methods for mRNA Isolation and cDNA Cloning", Biochemistry, vol. 26, pp. 1617–1625, 1987.

Vosberg et al. "Effect of Deoxynucleoside Phosphorothioates Incorporated in DNA on Cleavage . . . " JBC, vol. 257, pp. 6595–6599 (1982).

Krawinkel et al. (1986) "Rapid Synthesis of cDNA of Cloning," NAR, vol. 14, p. 1913.

Maniatis et al. (1982) "Molecular Cloning" CSH (New York) pp. 197–198.

Gruenbaum et al. (1981) "Restriction Enzyme Digestion of Hemimethylated DNA" NAR, vol. 9, pp. 2509–2515.

Nelson et al (1987). "The Effect of Site–Specific Methylation on Restriction–Modification Enzymes." NAR, vol. 15, pp. r219–r230.

*Primary Examiner*—David Guzo
*Attorney, Agent, or Firm*—Albert P. Halluin; Pennie & Edmonds LLP

[57] ABSTRACT

The present invention provides an improved method for the synthesis of double stranded DNA, particularly complementary DNA for the construction of directional complementary DNA libraries. The method comprises synthesizing a first strand of DNA complementary to a selected RNA or DNA template by contacting with the template a linker/primer comprising a selected restriction site, a suitable RNA or DNA dependent DNA polymerase, and substrates comprising a deoxyribonucleotide triphosphate analog. The linker/primer and deoxyribonucleotide triphosphate analog are selected such that incorporation of the nucleotide analog in the first strand substantially protects the double stranded DNA from cleavage, under conditions sufficient to cleave or substantially cleave the linker/primer, at the selected restriction site.

9 Claims, 3 Drawing Sheets

```
                    ········ RNA
                    ------ 5metC-DNA
                    ——— DNA primer/linker
      5' CTCGAGTTTTTTTTTTTT  3'
A     3'       AAAAAAAAAAAA ·······················5'

│ Moloney reverse transcriptase
                   │ 5-methyl dCTP
                   ↓ dATP,dGTP,dTTP XhoI
      5' CTCGAGTTTTTTTTTTTT  ------------------ 3'
B     3'       AAAAAAAAAAAA  ·················· 5'

│ RNase H
                   │ DNA Polymerase I
                   ↓ dNTPs

C     XhoI
      5' CTCGAGTTTTTTTTTTTT  ------------------ 3'
      3' GAGCTC AAAAAAAAAAAA ——————————— 5'

│ EcoRI Adaptors
                   ↓ T4 DNA Ligase

D  EcoRI                                              EcoRI
   5'AATTC···CTCGAGTTTTTTTTTTTT--------------···G    3'
   3'    G···GAGCTCAAAAAAAAAAAA ——————————···CTTAA 5'

│ XhoI Restriction Endonuclease
                   ↓

XhoI                                           EcoRI
      5' TCGAGTTTTTTTTTTTT  --------------···G    3'
      3'     C AAAAAAAAAAAA ——————————··· CTTAA 5'

Completed Directional cDNA
```

FIG. 1

FIG. 3
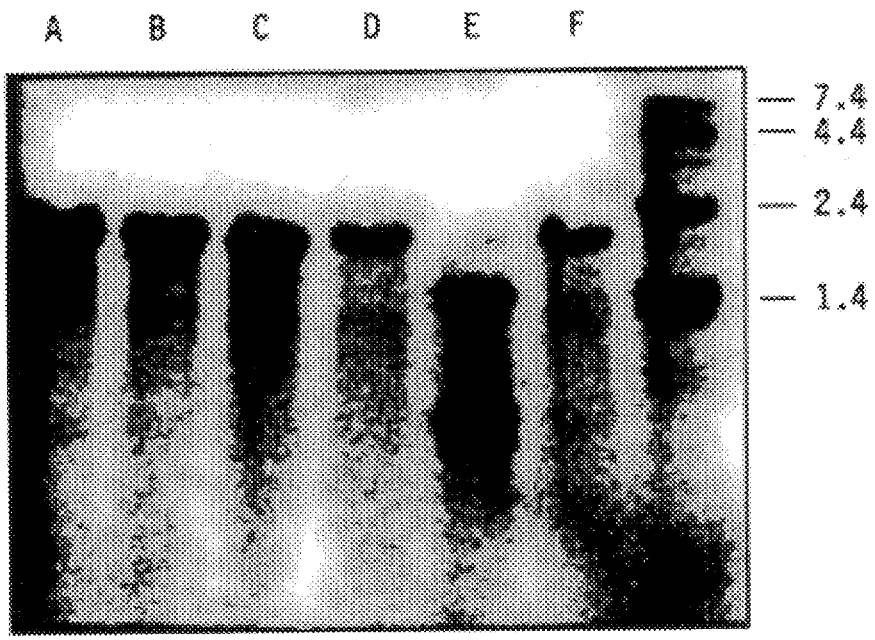
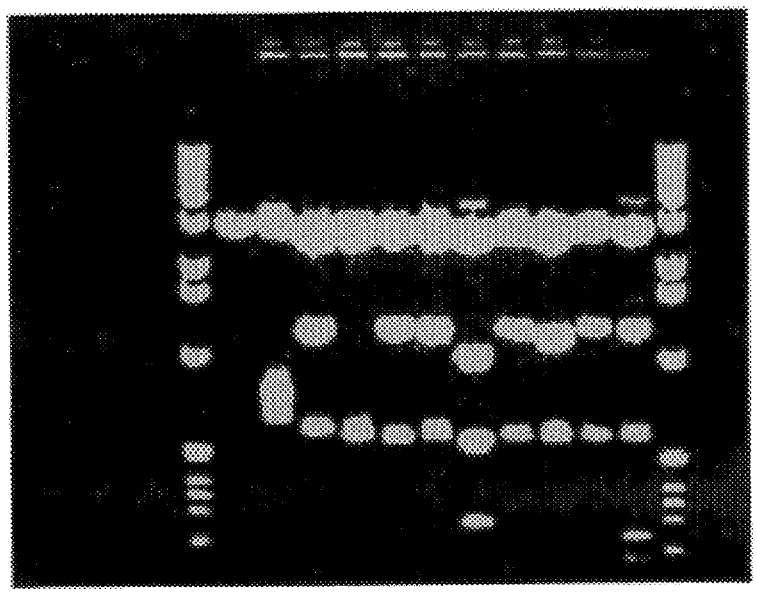
FIG. 4

METHOD OF DOUBLE STRANDED DNA SYNTHESIS

This is a continuation of application Ser. No. 07/981,931, filed on Nov. 23, 1992, now abandoned, which is a continuation of parent application Ser. No. 07/700,066, filed on May 2, 1991, now abandoned, which is a continuation of parent application Ser. No. 07/246,567, filed on Sep. 19, 1988, now abandoned.

FIELD OF THE INVENTION

The present invention relates to methods for DNA synthesis. More particularly, it relates to an improved method for the synthesis of double stranded DNA and the construction of directional DNA libraries.

BACKGROUND OF THE INVENTION

The synthesis of double stranded DNA, complementary to messenger RNA, and the insertion of this DNA into prokaryotic vectors is of fundamental importance to the molecular cloning and analysis of eukaryotic genes. The construction of complementary DNA libraries, i.e., bacteria or bacteriophage containing complementary DNA clones representative of a messenger RNA population, is often essential for a full understanding of gene expression and processing. Accordingly, the construction of directional libraries, in which complementary DNA is synthesized and ligated to a suitable vector, e.g., a plasmid or bacteriophage lambda vector, in a predetermined orientation to permit the expression of the inserted DNA, is highly desirable. Further, it is desirable that methods of complementary DNA synthesis permit the insertion of synthesized DNA into bacteriophage lambda vectors as such vectors generally have higher efficiencies than plasmid vectors for DNA library construction. See, Maniatis, T. et al, *Molecular Cloning: A Laboratory Manual*, Cold Spring Harbor Laboratory Publications, Cold Spring Harbor, N.Y. (1982).

A profusion of methods are presently available for the construction of complementary DNA libraries. See, e.g., Maniatis, T. et al, supra. However, the process remains difficult to master because methods of DNA library construction usually entail multiple sequential enzymatic reactions on small amounts of substrate. Methods of first strand complementary DNA synthesis relevant to the present invention rely upon the enzymatic synthesis of DNA from a nucleic acid template, e.g., messenger RNA. Enzymes capable of catalyzing the synthesis of DNA are referred to as "RNA dependent DNA polymerases" where the nucleic acid template is RNA and "DNA dependent DNA polymerases" where the template is DNA (generally, however, RNA dependent DNA polymerases are also capable of functioning as DNA dependent polymerases). More specifically, RNA dependent DNA polymerases such as AMV or MMLV reverse transcriptases are relied upon for the enzymatic synthesis of the first strand of complementary DNA from a messenger RNA template. Both types of DNA polymerases require, in addition to a template, a polynucleotide primer and deoxyribonucleotide triphosphates. The synthesis of first strand complementary DNA is usually primed with an oligo-d(T), consisting of 12-18 nucleotides in length, that initiates synthesis by annealing to the poly-A tract at the 3' terminus of eukaryotic messenger RNA molecules. However, other primers, including short random oligonucleotide primers, can be used to prime complementary DNA synthesis. During the polymerase reaction the primer is extended, stepwise, by the incorporation of deoxyribonucleotide triphosphates at the 3' end of the primer. Additionally, for optimal activity, DNA polymerases usually require magnesium and other ions to be present in reaction buffers in well defined concentrations.

Following synthesis of the first strand of complementary DNA, several methods can be employed to replace the RNA template with the second strand of DNA. One such method involves removal of the messenger RNA with NaOH and self-priming by the first strand of complementary DNA for second strand synthesis. Generally, the 3' end of single stranded complementary DNA is permitted to form a hairpin-like structure that primes synthesis of the second strand of complementary DNA by *E. coli* DNA polymerase I or reverse transcriptase. However, the method most commonly relied upon involves the replacement synthesis of second strand complementary DNA. See, Gubler, U. and Hoffman, B. J. (1983) *Gene* 25: 263-269. During replacement synthesis the product of the first strand synthesis, a complementary DNA: messenger RNA hybrid, provides a template and a primer for a nick-translation reaction in which the enzyme RNase H produces nicks and gaps in the messenger RNA strand, resulting in a series of RNA primers for synthesis of the second strand of complementary DNA with the enzyme *E. coli* DNA polymerase I.

After synthesis of a double stranded complementary DNA, the synthesized DNA must be introduced into a host cell, e.g., a bacterial strain, and replicated by means of a suitable vector such as a bacteriophage lambda vector. Several methods have been described and are presently available for ligation of double stranded complementary DNA to bacteriophage lambda vectors. See, e.g., Young, R. A., Davis, R. W. (1983) *Proc. Natl. Acad. Sci.* 80: 1194-1198; and Huynh, T. V., Young, R. A., Davis, R. W. (1985) in DNA Cloning Volume III, a practical approach, ed., D. M. Glover, *IRL Press*. Such methods involve, for example, the addition of short synthetic polynucleotide linkers which are ligated to the ends of the complementary DNA after second strand synthesis. The linkers contain sequences that are recognized by an appropriate restriction endonuclease, e.g., EcoR I. After the linkers have been ligated to the ends of the complementary DNA they are then cut with the appropriate restriction endonuclease to generate identical cohesive DNA sequences on both ends of the complementary DNA, thereby facilitating ligation of the complementary DNA to a bacteriophage lambda vector. Additionally, as complementary DNA clones of interest may contain restriction sites recognized by the restriction endonuclease, complementary DNA must usually be treated with a methylase, such as EcoR I methylase, prior to ligation of the synthetic linkers to protect the internal restriction sites from subsequent digestion. While such methods yield complementary DNA in bacteriophage lambda vectors and protect the complementary DNA of interest, the directionality of the DNA is not preserved. Thus, such methods fail to ensure that the synthesized complementary DNA will be inserted into a vector in the proper orientation to permit expression in a host cell.

Alternatively, methods have been described involving the sequential addition of linkers for the construction of complementary DNA libraries that preserve the directionality of the DNA clones of interest. See, e.g., Helfman, D. M., Feramisco, J. R., Fiddes, J. C., Thomas, G. P. and Hughes, S. H. (1983) *Proc. Natl. Acad. Sci. USA* 80: 31-35. Generally, however, presently available methods which preserve the directionality of complementary DNA rely upon methodology which is difficult to perform and tend to be either inefficient or ineffective for the construction of complementary DNA libraries in bacteriophage lambda vectors. As the introduction of a vector into a host strain is one of the least efficient steps in the construction of complementary DNA libraries, the inability to use bacteriophage lambda vectors, which generally have higher efficiencies than plasmid vectors, is an important limitation inherent in such methods.

Recently, a method has been developed for the construction of directional libraries in bacteriophage lambda vectors which involves the priming of first strand complementary DNA synthesis with a linker/primer. See, Krawinkel, U. and Zoebelein, R. (1986) *Nucl. Acids Res.* 14: 1913; and Han, J. H. and Rutter, W. J. (1987) Biochemistry 26: 1617–1625. The linker/primer is typically an oligonucleotide containing a restriction site sequence at the 5' end and an oligo-d(T) sequence at the 3' end of the molecule. After synthesis of the first and second strands of complementary DNA, an adaptor or second linker, containing a restriction site different from the linker/primer, is ligated to the ends of the complementary DNA. After ligation of the adaptor or second linker, the first restriction site contained within the linker/primer is cleaved, resulting in removal of the adaptor or second linker from the 3' end of the complementary DNA. The product of this method is, therefore, a complementary DNA molecule having different cohesive ends on each end of the molecule. Such a DNA molecule can thereafter be ligated to a vector that has been cleaved to generate compatible cohesive termini, permitting the insertion of the complementary DNA into the vector in an orientation to permit expression.

However, a significant limitation inherent in the foregoing method is that it is not possible to protect the complementary DNA of interest from restriction endonuclease digestion without also preventing cleavage of the linker/primer. Unlike methods in which linkers are added after second strand synthesis, the complementary DNA synthesized by the foregoing method cannot be methylated to protect it from digestion prior to addition of the linker/primer as the linker/primer is utilized to initiate first strand synthesis. Further, the treatment of the complementary DNA synthesized by this method would result in the protection of restriction sites within the linker/primer, and subsequent inability to cleave the adaptor or second linker from the 3' end to generate different cohesive termini for purposes of ligation. Therefore, if the double stranded complementary DNA contains one or more restriction sites identical to the restriction site in the linker/primer, the complementary DNA will be cleaved into fragments at the time it is prepared for ligation to a vector and, subsequently, only a portion of the desired DNA will be cloned. This undesired, but unavoidable, cleavage of complementary DNA molecules prior to ligation substantially increases the difficulty of isolating and analyzing complementary DNA molecules.

To alleviate the problems discussed above, the selection of a restriction enzyme, and corresponding restriction site in the linker/primer sequence, which rarely cleaves eukaryotic DNA has been suggested. However, the absence of a particular restriction site within the complementary DNA of interest cannot be presumed. Moreover, even rare restriction enzymes, such as Not I and Sal I, will potentially digest the complementary DNA of interest.

Although the problems enumerated above are not intended to be exhaustive, the limitations inherent in the methods presently available for the synthesis of complementary DNA and construction of directional DNA libraries are readily apparent. Accordingly, there exists a need for an improved method of construction of complementary DNA libraries which permits the insertion of complementary DNA in cloning vectors, particularly bacteriophage lambda vectors, in the orientation required for expression and protects the complementary DNA of interest from digestion by restriction endonucleases. Additionally, there exists a need for an improved method for the construction of directional DNA libraries that does not rely upon the presence or absence of specific nucleotide sequences in the complementary DNA of interest. The present invention meets these needs.

SUMMARY OF THE INVENTION

The present invention provides an improved method for the synthesis of double stranded DNA complementary to a selected RNA or DNA template wherein a predetermined orientation of the double stranded DNA is preserved. The method of the invention comprises synthesizing a first strand of DNA complementary to the selected template by contacting with the template, under conditions effective to permit the polymerization of the first strand, a polynucleotide linker/primer comprising a restriction site and being sufficiently complementary to the template to hybridize therewith, a suitable RNA or DNA polymerase and deoxyribonucleotide triphosphate substrates comprising a deoxyribonucleotide triphosphate analog.

In accordance with the invention, the linker/primer and deoxyribonucleotide triphosphate analog are selected such that the linker/primer is capable of being cleaved at said restriction site and the incorporation of the nucleotide analog in the first strand substantially protects the double stranded DNA from cleavage, under conditions sufficient to cleave or substantially cleave the linker/primer, at said restriction site.

The present invention is particularly useful for the synthesis of complementary DNA and the construction of directional DNA libraries. The advantages of the invention over prior art methods will become apparent after consideration of the accompanying drawings and the following detailed description of the invention.

BRIEF DESCRIPTION OF THE DRAWINGS

FIG. 1 is a schematic diagram of the construction of cDNA from mRNA showing: a) synthesis of first strand cDNA by reverse transcriptase and primed with a linker/primer, dATP, dGTP, dTTP, and 5-methyl-dCTP replacing dCTP; b) second strand cDNA synthesis by nick translation of the RNA strand; c) ligation of EcoR I adaptors to both ends of the double stranded cDNA; d) cDNA cleaved at the Xho I site in the linker/primer for ligation of the cDNA into a bacteriophage vector.

FIG. 3 demonstrates synthesis of first and second strand cDNA with dCTP as compared to 5-methyl-dCTP replacing dCTP during first strand synthesis. The template was a 1.8 kilobase polyadenylated template. Lanes A and B compare the length of the first strand synthesis with (shown in lane B) and without (shown in lane A) 5-methyl-dCTP. The synthesis using 5-methyl-dCTP is as efficient as with dCTP. Lanes C and D demonstrate that the Second strand synthesis proceeds without significant degradation of the first strand for both methylated (lane D) and unmethylated (lane C) first strand cDNA. The last two lanes demonstrate that the unmethylated double stranded cDNA is cleaved (lane E) with Xho I under conditions which cannot cleave the cDNA that has incorporated 5-methyl-dCTP (lane F) during first strand synthesis.

FIG. 4 illustrates an agarose gel analysis of cDNA clones constructed from a 1.8 kb polyA RNA which contained a sequence that results in an Xho I site in the cDNA, constructed as described in Example 4. Most of the clones as seen in lanes A–J have two bands which indicate that the Xho I site in the cDNA was not cleaved as a result of Xho I digestion of the linker/primer during preparation of the cDNA for ligation to the vector.

DETAILED DESCRIPTION OF THE INVENTION

Figure 2:
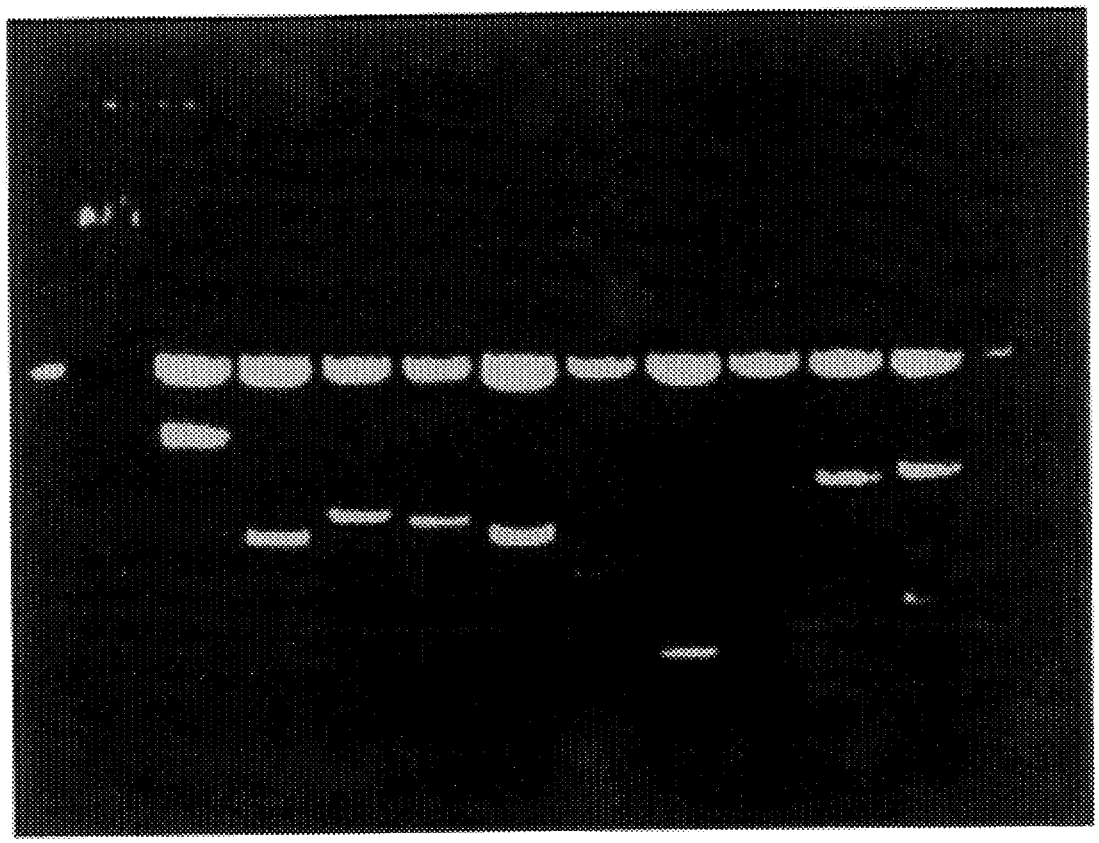
FIG. 2 illustrates an agarose gel analysis of the cDNA inserts of ten cDNA clones which were chosen at random from the directional cDNA library constructed as described in Example 1. Ten clones were picked and the cDNA inserts were excised in the pBluescript™ SK- plasmid as described in Example 2. DNA size markers are shown in the lane to the left of lane A. Lanes A–K show Xho I-EcoR I double digests of the excised plasmids. The upper band is the vector and the lower band in each lane is the cDNA insert.

As indicated above, the present invention provides an improved method for the synthesis of double stranded DNA complementary to a selected RNA or DNA template wherein a predetermined orientation of the double stranded DNA is preserved. In accordance with the invention, a first strand of DNA complementary to the RNA or DNA template is synthesized by contacting with the template, under conditions effective to permit the polymerization of the first strand, a polynucleotide linker/primer comprising a restriction site, a suitable RNA or DNA dependent DNA polymerase and deoxyribonucleotide triphosphate substrates comprising a deoxyribonucletide triphosphate analog. The linker/primer is selected to be sufficiently complementary to the template to hybridize with the template and permit the initiation of DNA synthesis. Further, the linker/primer and the deoxyribonucleotide triphosphate analog are selected such that the linker/primer is capable of being cleaved at said restriction site and the incorporation of the nucleotide analog in the first strand substantially protects the double stranded DNA from cleavage, under conditions sufficient to cleave or substantially cleave the linker/primer, at said restriction site.

As used herein, the term "primer" refers to a polynucleotide which is capable of hybridizing with an RNA or DNA template to permit the initiation of DNA synthesis under appropriate conditions, i.e., in the presence of a suitable RNA or DNA dependent DNA polymerase and deoxyribonucleotide triphosphate substrates and at a suitable temperature and pH. For example, oligo-d(T) 18 is a suitable primer to initiate DNA synthesis on a messenger RNA template having a poly(A) tract at the 3' end of the molecule. The term "linker", as used herein, refers to a polynucleotide comprising at least one restriction site, i.e., a specific nucleotide sequence which is a recognition site for a restriction endonuclease. For example, an oligonucleotide containing the sequence 5'CTCGAG 3', which is recognized by the restriction endonuclease Xho I, can be utilized as a linker. Additionally, for purposes of the present invention, the term "restriction endonuclease" includes restriction enzymes, restriction endonucleases and other site specific endonucleases capable of cleaving or substantially cleaving DNA at or near a specific nucleotide sequence.

In the context of the present invention, the term "linker/primer" refers to a polynucleotide comprising sequences capable of functioning both as a linker and as a primer. The nucleotide sequences comprising the linker portion of the linker/primer can either be overlapping with or separable from the nucleotide sequences comprising the primer portion of the linker/primer. Preferably, the linker/primer comprises an oligonucleotide, consisting of approximately 12–60 nucleotides in length. It will be appreciated, however, that the length of the linker/primer can vary provided that it is sufficiently long to prime the synthesis of a first strand of DNA. Additionally, it is preferred that the primer portion of the linker/primer comprise an oligo-d(T) where the template is polyadenylated RNA, e.g., messenger RNA. However, the primer portion of the linker/primer may comprise a mixture of random nucleotide sequences. Generally, the linker/primer is a single stranded molecule; however, the linker portion of the linker/primer can be double stranded.

Linker/primers suitable for use in the invention can be produced synthetically by conventional techniques well known in the art. However, naturally occurring linker/primers obtained, for example, by enzymatic modification of DNA isolated from bacterial or other natural sources, can be utilized in the invention. Additionally, in a preferred embodiment of the invention, the linker/primer is immobilized and bound to a solid support. DNA synthesis on a solid support, in accordance with the present invention, facilitates the purification of desired reaction products and is particularly advantageous where multiple sequential reactions are required, e.g., during the synthesis of complementary DNA. Methods for immobilizing oligonucleotides which can function as linker/primers have been described in European Patent Publication PCT/US87/01966, the disclosure of which is incorporated by reference herein. Alternatively, the linker/primer utilized in the invention can be in solution.

For purposes of the present invention, the linker/primer is selected such that the primer portion of the linker/primer is sufficiently complementary to a selected RNA or DNA template to hybridize therewith. To be sufficiently complementary, all of the nucleotide sequences comprising the primer portion of the linker/primer need not be complementary to the template at every nucleotide position, e.g., non-complementary nucleotide sequences can be attached to the 5' end of the primer sequence, with the remainder of the primer sequence being complementary to the template. Additionally, non-complementary sequences can be interspersed within the primer portion of the linker/primer provided that the primer sequence is sufficiently complementary to the template to initate DNA synthesis in the presence of a suitable RNA or DNA dependent DNA polymerase and deoxyribonucleotide triphosphate substrates.

In accordance with the invention, the selection of a suitable restriction site in the linker portion of the linker/primer will be dependent upon the selection of deoxyribonucleotide triphosphate analogs, as described herein, for incorporation into the first strand of the double stranded DNA to be synthesized. Preferably, a single restriction site is selected; however, the linker/primer may contain two or more restriction sites. Preferred for use in the invention is a linker/primer comprising an Xho I restriction site. Also preferred for use is a linker/primer comprising an Spe I restriction site. However, it will be understood that as the restriction site or sites contained within the linker/primer are used to generate cohesive ends suitable for ligation of the synthesized DNA to a desired vector, alternative restriction sites can be selected provided a suitable combination of nucleotide analog, linker/primer and vector can be chosen. Accordingly, the present invention is not limited to the use of any particular restriction site or sites within the linker/primer.

In the context of the present invention, the term "deoxyribonucleotide triphosphate analog" refers to an analog of the deoxyribonucleotide triphosphates dATP, dCTP, dGTP and dTTP which is capable of being incorporated into double stranded DNA as a nucleotide analog during chain extension by RNA or DNA dependent DNA polymerase specifically at positions complementary to only one nucleotide base, i.e., adenosine, thymidine, cytosine or guanosine, in the template. The term "nucleotide analog", as used herein, refers to a deoxyribonucleotide monophosphate analog incorporated into DNA during synthesis with a deoxyribonucleotide triphosphate analog substrate. For example, the deoxyribonucleotide triphosphate analog 5-methyl-deoxyribocytosine- 5'-triphosphate (5-methyl dCTP), will be incorporated into synthesized DNA as the nucleotide analog 5-methyl-deoxyribocytosine-5'-monophosphate (5-methyl dCMP) at positions complementary to guanosine in the template strand but not at positions complementary to adenosine, cytosine or thymidine. Generally, the deoxyribonucleotide triphosphate analogs useful in the present invention are analogs of the alpha-phosphate and/or deoxribonucleotide components of deoxyribonucleotide triphosphates.

In accordance with the invention, the deoxyribonucleotide triphosphate analog selected for use is capable of protecting the double stranded DNA in which the nucleotide analog is incorporated from cleavage by at least one restriction endonuclease. Preferred for use in the invention are deoxyribonucleotide triphosphate analogs which are methylated deoxyribonucleotide triphosphates. Also preferred for use are alpha-thio-deoxyribonucleotide triphosphate analogs. Particularly preferred for use is 5-methyl-deoxyribocytosine-5'-triphosphate. However, the present invention comtemplates the use of a multitude of possible deoxyribonucleotide triphosphate analogs, including 2'-deoxyriboinosine-5'-triphosphate, 5-iodo-2'-deoxyribocytosine-5'-triphosphate, 5-mecuri-2'-deoxyribouridine-5'-triphosphate, and 7-methyl-2'-deoxyriboguanosine-5'-triphosphate. Accordingly, those skilled in the art will appreciate that alternative deoxyribonucleotide triphosphate analogs may be suitably utilized in the invention provided that such analogs are capable of being specifically incorporated within and protecting double stranded DNA from cleavage by restriction endonuclease activity and does not prevent replication of the DNA in host cells.

Further in accordance with the invention, the deoxyribonucleotide triphosphate analog and linker/primer are selected such that the incorporation of the nucleotide analog in double stranded DNA substantially protects the synthesized DNA from cleavage, under conditions sufficient to cleave or substantially cleave the linker/primer, at the selected restriction site. It will be understood, however, that certain restriction endonucleases recognize a multiplicity of nucleotide sequences. Accordingly, the present invention contemplates the selection of deoxyribonucleotide triphosphate analogs capable of protecting synthesized DNA from cleavage at nucleotide sequences identical to the restriction site contained within the linker/primer as well as at other specific nucleotide sequences which are recognition sites for the restriction endonuclease selected to cleave the linker/primer. In a particularly preferred embodiment of the invention, the nucleotide analog selected for use is 5-methyl-deoxycytosine-5'-triphosphate (5-methyl dCTP) and the linker/primer is an oligonucleotide wherein the linker portion of the linker/primer comprises an Xho I or Spe I restriction site.

For purposes of the present invention, the nucleotide analog substantially protects the synthesized DNA if the selected restriction site in the linker/primer can be cleaved or substantially cleaved under appropriate conditions at a rate which is appreciably greater than the rate at which the synthesized DNA incorporating the nucleotide analog can be cleaved. The linker/primer will be substantially cleaved if at least 80% of the synthesized double stranded DNA molecules are cleaved at the selected restriction site within the linker/primer by a suitable restriction endonuclease under appropriate conditions. It will be appreciated that complete protection of the synthesized DNA is not required and that the differential cleavage of the linker/primer and the DNA of interest permits a substantial portion of the DNA molecules to be obtained as full length clones. Accordingly, the substantial protection provided by the method of the the present invention greatly facilitates the isolation and analysis of certain DNA clones.

Deoxyribonucleotide triphosphate analogs suitable for use in the present invention are generally available commercially. In addition, such analogs can be prepared synthetically or by chemical modification of deoxyribonucleotide triphosphates by techniques well known in the art. Alternatively, deoxyribonucleotide triphosphate analogs can be isolated from natural sources by standard techniques, e.g., 5-methyl-deoxyribocytosine- 5'-monophosphate can be obtained from mammalian chromosomal DNA.

A determination of the suitability of deoxyribonucleotide triphosphate analogs for use in the present invention can be accomplished by conventional techniques well known in the art. For example, standard gel electrophoresis of products of the primer extension with a desired analog and an RNA or DNA dependent polymerase can be relied upon to determine whether a nucleotide analog is incorporated during DNA synthesis. In addition, restriction digestion of the products of the primer extension by standard procedures can be used to determine if DNA synthesized with a desired analog is substantially protected from cleavage by a restriction endonuclease at restriction sites in which the nucleotide analog is incorporated. Further, DNA synthesis on RNA and DNA templates may require different DNA polymerases. These polymerases may vary in their ability to synthesize DNA with specific deoxyribonucleotide triphosphate analogs. The suitability of specific analogs for use with a desired DNA polymerase may be determined by standard primer extension assays of the desired analog and the specific DNA polymerase to be used for DNA synthesis.

The method of the present invention can employ any RNA or DNA template desired for use for which a linker/primer can be constructed and used to prime DNA synthesis. The present invention is particularly useful for the synthesis of complementary DNA and the construction of directional libraries where the template is polyadenylated RNA, e.g., messenger RNA, and the linker/primer comprises an oligo-d(T). However, it is anticipated that suitable linker/primers can be constructed for use with RNA or DNA obtained or derived from any source, including RNA or DNA isolated from prokaryotes and eukaryotes. If double stranded DNA is to be used as the template, the two strands of the double stranded molecule must first be separated, preferably by denaturation of the strands by physical, chemical or enzymatic means.

In accordance with the invention, suitable RNA or DNA dependent DNA polymerases are relied upon for the enzymatic synthesis of DNA complementary to an RNA or DNA template to produce double stranded DNA either directly from a DNA template or indirectly from an RNA template by replacement of the RNA strand and synthesis of a second strand of DNA. Suitable enzymes for use in of the invention include, for example, reverse transcriptases such as avian myoblastoid virus (AMV) reverse transcriptase and murine moloney leukemia virus (MMLV) transcriptase, *E. coli* DNA polymerase I, the Klenow fragment of *E. coli* DNA polymerase I, T4 DNA polymerase and other available enzymes which will induce the synthesis of DNA complementary to an RNA or DNA template. Preferably, where messenger RNA is the template, reverse transcriptases are relied upon for the enzymatic synthesis of DNA complementary to the template.

The synthesis of the second strand of the double stranded DNA can be accomplished by standard methods known in the art. Preferably, second strand synthesis is accomplished by replacement synthesis techniques using the enzymes RNAase H and DNA polymerase I and deoxyribonucleotide triphosphates as described in Gubler, U. and Hoffman, B. J. (1983) *Gene* 25: 263–269. Alternatively, the RNA strand can be removed with NaOH or other suitable reagent by standard procedures, and second strand synthesis can be primed with a hairpin-like structure forming at the 3' end of the first strand of DNA. Such a method is described in Helfman, D. M., Feramisco, J. R., Fiddes, J. C., Thomas, G. P. and Hughes, S. H. (1983) *Proc. Natl. Acad. Sci. USA* 80: 31–35. Those skilled in the art will appreciate, however, that a multitude of methods for second strand synthesis may be used in combination with the improved method of the present invention.

After second strand synthesis of the double stranded DNA, cohesive termini are generated for purposes of ligating the synthesized DNA to a suitable vector, preferably a bacteriophage lambda vector. Since the DNA resulting from synthesis has both 5' and 3' termini at each end, the end of the double stranded DNA molecule which corresponds to the 3' end of the template will be referred to as the 3' end of the double stranded DNA. The end of the double stranded DNA that corresponds to the 5' end of the template will be referred to as the 5' end. Standard techniques can be relied upon to generate a cohesive nucleotide sequence at the 5' end of the double stranded DNA compatible with the terminus of a desired lambda phage vector that has been prepared by cleavage with a restriction endonuclease. For example, Bahl, C. P., Wu, R., Brousseau, R., Sood, A. K., Hsiung, H. M. and Narang, S. A. (1978) *Biochem. Biophys. Res. Commun.* 81: 695 describes the use of adaptors, such as EcoR I adaptors, which when ligated to double stranded DNA in the presence of a suitable ligase, such as T4 DNA ligase, form termini that are cohesive to ends of a desired lambda phage vector after cleavage. Generally, the adaptors suitable for use are oligonucleotide pairs complementary to one another and selected such that blunt and cohesive ends are formed upon hybridization of the pairs. The cohesive end formed by the adaptor is compatible with the cohesive end formed by cleavage of a suitable vector with a restriction endonuclease. Additionally, ligation efficiency may be enhanced by phosphorylation of the adaptors, e.g., by a T4 DNA kinase, after ligation to the complementary DNA. Alternatively, second linkers can be ligated to the double stranded DNA as described by Maniatis, T. et al, supra. If second linkers are used, they are thereafter cleaved with an appropriate restriction endonuclease to generate an overhang compatible with that of the vector desired for use.

Additionally, if the double stranded DNA is not substantially protected from digestion by the restriction endonuclease used to cleave the second linkers, the double stranded DNA should be treated with an appropriate methylase prior to ligation of the second linkers. Methods for protecting DNA with methylases are well known and are described, for example, in Gubler, U. and Hoffman, B. J. (1983) *Gene* 25: 263–269.

The linker/primer attached to the 3' end of the DNA is cleaved at the selected restriction site by a suitable restriction endonuclease under appropriate conditions. The double stranded DNA, synthesized as described herein, is substantially protected from cleavage by the restriction endonuclease used to cleave or substantially cleave the linker/primer. Preferably, the linker/primer is cleaved at an Xho I or Spe I restriction site for ligation to a vector. The resulting DNA contains, therefore, an Xho I or Spe I compatible overhang on the 3' end of the DNA and, for example, an EcoR I compatible overhang on the 5' end. In a preferred embodiment of the invention in which the linker/primer is bound to a solid phase, cleavage of the linker/primer at the selected restriction site separates the synthesized DNA from the solid phase.

Vectors suitable for ligation of double stranded DNA, synthesized in accordance with the present invention, contain restriction sites which after cleavage are compatible with the cohesive termini of the double stranded DNA. Bacteriophage lambda vectors, preferably containing an Xho I and/or Spe I restriction site, are particularly useful for the construction of directional DNA libraries. Additionally, it is desirable that the vector include an RNA Polymerase promoter and/or other regulatory sequences functionally associated with the 5' end of the double stranded DNA inserted into the vector to permit the transcription and translation of the inserted DNA sequences. Suitable vectors are commercially available or can be constructed by techniques known in the art. See, Short, J. M. et al (1988) *Nucl. Acids Res. Vol* 16: 7583–7600; and Han, J. H. and Rutter, W. J. (1987) *Biochemistry* 26: 1617–1625.

Vectors in which the double stranded DNA is ligated can be introduced into an appropriate host cell by standard techniques, for example, by transformation or infection, to permit replication of the inserted DNA. Such methods are described by Maniatis T., et al, supra. It should be noted, however, that certain host cells express proteins which recognize and degrade DNA incorporating certain nucleotide analogs. For example, strains of *E. coli* which express mcrA or mcrB protein recognize and degrade DNA incorporating 5-methyl dCMP. The identification of suitable host cells can be accomplished by transformation or infection with DNA incorporating the nucleotide analog as compared to normal DNA.

Further in accordance with the present invention, a kit is provided for the synthesis of a double stranded DNA from a selected RNA or DNA template wherein a predetermined orientation of the double stranded DNA is preserved. The kit comprises a polynucleotide linker/primer comprising a restriction site and being sufficiently complementary to the template to hybridize therewith, and at least one deoxyribonucleotide triphosphate analog. The linker/primer and deoxyribonucleotide triphosphate analog are selected such that the linker/primer is capable of being cleaved at said restriction site and the incorporation of the nucleotide analog in a first strand of double stranded DNA substantially protects the double stranded DNA from cleavage, under conditions sufficient to cleave or substantially cleave the linker/primer, at said restriction site. Preferably, the linker/primer component of the kit is bound to a solid support.

In a preferred embodiment of the invention for synthesis of double stranded complementary DNA, the kit comprises an oligonucleotide linker/primer comprising an Xho I restriction site and being sufficiently complementary to a selected messenger RNA template to hybridize therewith, and 5-methyl dCTP. The linker/primer and 5-methyl dCTP are selected such that the linker/primer is capable of being cleaved at the Xho I site and the incorporation of 5-methyl dCMP in a first strand of double stranded DNA substantially protects the double stranded DNA from cleavage, under conditions sufficient to cleave or substantially cleave the linker/primer, at the Xho I site.

As indicated above, the present invention is particularly useful for complementary DNA synthesis from a messenger RNA template and the construction of directional complementary DNA libraries. As the present invention permits the construction of directional complementary DNA libraries in bacteriophage lambda vectors and substantially protects complementary DNA of interest from restriction endonuclease activity, the present invention overcomes the limitations inherent in prior art methods for complementary DNA synthesis and library construction. Additionally, the present invention is advantageous in that it does not rely upon the presence or absence of any particular nucleotide sequence in the complementary DNA of interest. Further, the invention, being readily adaptable to solid phase synthesis, enables the use of a linker/primer for complementary DNA synthesis more effectively than prior art methods.

The construction of directional complementary DNA libraries is useful for the isolation and analysis of complementary DNA molecules by standard antibody screening procedures. Specifically, antibodies directed against proteins expressed by the complementary DNA can be used to screen the complementary DNA library and isolate the desired complementary DNA clones. Additionally, methods that rely upon the identification of functional proteins expressed in *Xenopus oocytes* injected with RNA transcripts derived from complementary DNA clones are enhanced by the present invention because the production of anti-sense RNA transcripts is minimized.

The following examples are offered to further illustrate the present invention and are not intended to limit the invention in any way.

The oligonucleotide linker/primer used in the examples to synthesize complementary DNA and construct directional complementary DNA libraries was (5' GAGAGAGAGAGCTCGAATTCTCTAGACTCGAGTTTTTTTTTTTTTTTTTT 3'). The deoxyribonucleotide triphosphate analog used in the examples was 5-methyl-deoxyribocytosine-5'-triphosphates.

EXAMPLE 1

CONSTRUCTION OF DIRECTIONAL COMPLEMENTARY DNA LIBRARY

Synthesis of First Strand Complementary DNA

A schematic diagram of the steps performed for synthesis of cDNA in this example is shown in FIG. 1. The template for first strand synthesis was 5 μg of poly(A)+ RNA isolated from twenty murine diaphragms. Total RNA, which consists of a mixture of ribosomal RNA, transfer RNA and messenger RNA was prepared essentially as described by Chomczynski, P. and Sacchi, N. (1987) *Analytical Biochemistry* 162: 156–159. The RNA was further enriched for mRNA sequences by oligo-d(T) chromatography as described in Maniatis, T., et al, *Molecular Cloning: A Laboratory Manual*, Cold Spring Harbor Laboratory Publications, Cold Spring Harbor, N.Y. (1982). The oligonucleotide linker/primer (5' GAGAGAGAGAGCTCGAATTCTCTAGACTCGAGTTTTTTTTTTTTTTTTTT 3') was synthesized on an Applied Biosystems, Inc. (Foster City, Calif.) Oligonucleotide Synthesizer (model 361A) using chemicals supplied by the manufacturer. This oligonucleotide was used to prime first strand DNA synthesis. First strand synthesis was carried out in the presence of 20 units of RNase Block (Stratagene, La Jolla, Calif.), 10 mM dithiothreitol, 50 mM Tris-Base (pH 8.3), 75 mM KCl, 3 mM $MgCl_2$, 10.4 μg of linker/primer, 500 mM dATP, dGTP, dTTP, 500 mM of 5-methyl-dCTP (Pharmacia, Piscataway, N.J.) and 40 units of MMLV reverse transcriptase (Stratagene, La Jolla, Calif.) in a final volume of 50 μl. The synthesis was allowed to continue for 1.5 hours at 37° C. The products of the reaction were separated on Trisacryl GF-05 M (IBF Biotechnics, VillenenveLa Garenne, France) which had been equilibrated in 1X STE (10 mM Tris-Base (pH 8.0), 100 mM NaCl, 1 mM EDTA) by spin column chromatography. The spin column was centrifuged at a speed setting of 75 on a DYNAC table-top centrifuge (Clay Adams, Parsippany, N.J.) at room temperature for 5 minutes. The column was washed with an additional 50 μl of 1X STE and the two eluants combined. First strand cDNA-RNA hybrids were ethanol precipitated on ice for 30 minutes and microfuged at 14000 rpm for 30 minutes at room temperature. The supernatant was removed and the pellet washed with 80% ethanol and dried under vacuum. The dry pellet was resuspended in a mixture of 40 μl of 10× second strand buffer (10× Buffer=250 mM Tris-base (pH 8.3), 1M KCl, 50 mM $MgCl_2$, 50 mM dithiothreitiol) and 322.93 μl of water.

Synthesis of Second Strand Complementary DNA

Second strand cDNA was synthesized in the presence of 150 mM dCTP, dGTP, dTTP and 75 mM cIATP with (Pharmacia, Piscataway, N.J.) 0.1 mCi of $\alpha$-$^{32}$P dATP (specific activity 800 Ci/mMol) (NGN), 100 units of *E. coli* DNA Polymerase I (Stratagene, La Jolla, Calif.) and 2.8 units of RNase H (BRL, Gaithersburg, Md.) in a final volume of 400 μl. The reaction was incubated at 16° C. for 2 hours, phenol extracted and ethanol precipitated. Pellets were washed with 80% ethanol and dried under vacuum. The pellet was resuspended in 10 μl of 5 T.1E. (5 mM Tris-Base (pH 7.5), 0.1 mM EDTA) and 4.75 μl was removed for T4 DNA polymerase blunting. The reaction was performed using a buffer consisting of 50 mM Tris-Base (pH 8.3), 10 mM $MgCl_2$, 10 mM DTT and 50 mM NaCl and 10 units of T4 DNA Polymerase (Stratagene, La Jolla) for 2 minutes at 37° C. and then all four of the deoxynucleotides were added to a concentration of 50 μM and the reaction was allowed to continue at 37° C. for 28 minutes. The enzyme reaction was stopped by adding EDTA to a final concentration of 20 mM after which the entire reaction was phenol extracted two times and ethanol precipitated. The pellet was washed in 80% ethanol, dried under vacuum and resuspended in 3.45 μl of the Sma I/Eco RI adaptor (5' AATTCCCGGG 3') (NEB, Beverly, Mass.) and 2.15 μl of the Sma I adaptor (5' pCCCGGG 3') (NEB, Beverly, Mass.) both of which were at a concentration of 1 mg/ml. The cDNA and adaptors were ligated together by adding 2 Weiss Units of T4 DNA ligase (Stratagene, La Jolla, Calif.) to the reaction in the presence of 50 mM Tris-HCl (pH 8.0), 7 mM $MgCl_2$, 1 mM dithiothreitol and 1 mM ATP in a final volume of 8 μl for 40 hours at 4° C. The ligase was heat killed at 70° C. for 30 minutes after which the reaction was brought to 20 ml of 50 mM Tris-HCl (pH 8.0), 7 mM $MgCl_2$, 2.0 mM ATP, 3.75 mM fresh dithiothreitol and 10 units of T4 polynucleotide kinase (Stratagene, La Jolla, Calif.). The reaction was allowed to proceed for 30 minutes at 37° C. after which the kinase was heat killed at a temperature of 70° C. for 30 minutes. Modification of the existing buffer to a final concentration of 105 mM NaCl, 6 mM β-mercaptoethanol, 10 mM $MgCl_2$ in a total volume of 50 μl with 400 units of Xho I (Stratagene, La Jolla, Calif.) caused the linker/primer to be digested away from the 3' end of the cDNA leaving the 5' end with its Eco RI adaptor intact. The restriction digest was run for 2 hours at 37° C. after which the cDNA was ethanol precipitated with 5 µg of tRNA (Sigma Chemicals, St. Louis, Mo). The microfuged pellet was washed in 80% ethanol and dried under vacuum after which it was resuspended in 5 µl of 1X STE, 1 µl sterile glycerol and 1 µl of saturated bromphenol blue. The sample was loaded on to a Sepharose CL-4B (Pharmacia, Piscataway, N.J.) column which was prepared by adding 1X STE equilibrated, defined sepharose CL-4B to a disposable plastic 1 ml pipet, the tip of which had been plugged with a small amount of sterile cotton and had been pre-run for at least 5 hours. Radioactivity eluting from the column was collected in 2 drop fractions.

Ligation of Double Stranded cDNA to Lambda Vector

The majority of the first four fractions of each sample (a total of 155 µl) were combined and phenol extracted before 10 µg of the Lambda Zap™ II vector (Stratagene, La Jolla, Calif.) (which had been cut with EcoR I and Xho I, dephosphorylated, phenol extracted, ethanol precipitated and resuspended in 5T.1E. to a concentration of 1 mg/ml) were added to the cDNA, mixed and ethanol precipitated. The pellet was washed in 80% ethanol and dried under vacuum before being resuspended in 3.5 µl of $H_2O$ and brought to a final concentration of 1 mM ATP 50 mM Tris-HCl (pH 8.0), 7 mM $MgCl_2$, 1 mM dithiothreitol and 2 Weiss Units of T4 DNA ligase (Stratagene, La Jolla, Calif.) in a final volume of 5 µl. The ligation was allowed to proceed for 16 hours at 4° C. before being transferred to room temperature for 1.5 hours. 1 µl of the 5 µl ligation was packaged in Gigapack Gold in vitro lambda phage packaging extract (Stratagene, La Jolla, Calif.), using the recommended protocol. The remaining 4 µl were diluted with an equal volume of 5T.1E. and each microliter was packaged separately in Stratagene's Gigapack Gold in vitro packaging extract. All packaging reactions were combined and the total library was titered with 200 µl of WB13 (Stratagene, La Jolla, Calif.) O.D. 600=0.5 in 3 ml of NZY top agar (0.7%) on NZY plates. 12.5 million recombinant phage were obtained, demonstrating the present invention to be an efficient method of cDNA synthesis.

EXAMPLE 2

This example demonstrates that the cDNA library, constructed as described in Example 1, contains cDNA inserts.

The murine diaphragm cDNA library cloned in the Lambda Zap™ vector (Stratagene, La Jolla, Calif.) was characterized to determine the average size of the cDNA insert. Analysis of clones in the Lambda Zap™ vector was easily accomplished following excision from the vector of the pBluescript(SK-) plasmid (Stratagene, La Jolla, Calif.) containing the clone. Excision was accomplished as described in Short, J. M. et al., (1988) *Nucl. Acids Res. Vol* 16: 7583–7600. Phage from the library constructed in the Lambda Zap™ vector were plated onto WB13 cells grown overnight at 37° C. in 1×TB media (1% Bacto-Tryptone, 0.5% NaCl) with 0.4% maltose and 20 mM $MgSO_4$, gently pelleted by centrifugation and resuspended in 10 mM $MgSO_4$. Ten well isolated plaques were cored from the titration plates and rescued in XL1-Blue cells. After excision of the cDNA in the pBluescript (SK-) plasmid, the XL1-Blue cells containing plasmid were spread on LB ampicillin plates and incubated overnight at 37° C. Isolated colonies were cultured in 1X Mombo broth with 100 µg/ml of ampicillin for 16 hours at 37° C. The cultures were centrifuged and a mini-prep of the plasmid DNA was prepared by the alkaline-lysis technique described in Maniatis, T. et al., supra. The pBluescript SK M13- plasmid DNA consisting of the vector and cDNA insert were digested with 10 units of Xho I and EcoR I (Stratagene, La Jolla, Calif.) in 105 mM NaCl, 10 mM $MgCl_2$, 50 mM Tris-base (pH 7.8) in a total volume of 10 µl for 2 hours at 37° C. All samples were analyzed by 1% agarose gel electrophoresis and in 1× TBE and in the presence of ethidium bromide.

As shown in FIG. 2, the results of the gel electrophoresis analysis confirmed that nine of ten recombinant phage contained recombinant clones. These cloned inserts are flanked by EcoR I and Xho I restriction sites. The clones ranged in size from 500 to 2500 base pairs. Two of the clones contained either an EcoR I or Xho I restriction site.

EXAMPLE 3

This example demonstrates that the cDNA library constructed in Example 1 contains the cDNA clones expected to be included in the library.

The library constructed in Example 1 was shown to contain clones encoding for actin proteins; known to be expressed in the murine diaphragms. The mouse diaphragm cDNA library constructed in Example 1 was screened for actin by plating 38,500 pfu on 0.4 ml of WB13 cells (O.D. 600=0.5) which had been prepared as described above. The infected cells were plated in 6 ml of NZY top agar onto 150 mm NZY plates. The plates were incubated for 12 hours at 37° C. and refrigerated for 1 hour prior to the sequential application and the simultaneous removal of two nitrocellulose BA85 (Schleicher & Schuell, Keenee, N.H.) filters. The phage clones in the plaque lifts were denatured in 1.5 M NaCl, 0.5M NaOH for 45 seconds with gentle scrubbing, then neutralized in 1.5M NaCl, 0.5M Tris-base (pH 8.0), and rinsed in 2× SSC 0.2M Tris-base (pH 7.5) as described in Maniatis, T., et al, supra. The filters were air dried and the DNA permanently bound by ultra-violet crosslinking with the Stratalinker crosslinking apparatus (Stratagene, La Jolla, Calif.) on a setting of 1200 µjoules. The filters were prehybridized with gentle agitation for 2 hours at 42° C. in prehybridization mixture consisting of 50 ml of 5× SSC, 40 mM NAPO4 (pH 6.5), 5× Denhardt's Solution, 0.1 mg/ml denatured salmon sperm DNA, 5% Dextran Sulfate, 50% formamide. Digestion of 10 µg of the plasmid pRβA-1, obtained from Dr. Peter Gunning (University of California at San Diego, San Diego, Calif.), with 45 units of Bgl I (Stratagene, La Jolla, Calif.) using the manufacturer's recommended buffer for two hours at 37° C. cleaved the plasmid into three fragments. The fragments were isolated by agarose gel electrophoresis and the 1200 base pair fragment was eluted on to NA-45 DEAE membrane (Schleicher & Schuell, Keene, N.H.) as specified in the manufacturer's instructions. Sixty nanograms of the purified fragment was labelled using the Oligo labelling kit (Pharmacia, Piscataway, N.J.) according to the manufacturer's instructions. Unincorporated nucleotides were removed using a 1× STE equilibrated Trisacryl GF-05 M (IBF Biotechnics, Villenenve-La Garenne, France) spin column. The probe ($1.8 \times 10^7$ cpm) was boiled for five minutes and added to the 15 ml of the prehybridization mixture and incubated for 16 hours at 42° C. with gentle agitation. The hybridization mixture was removed and the probe was washed for 2 hours at 68° C. in three changes of 6× SSC, 0.1% SDS, then for 2 hours at 45° C. in three changes of 0.1× SSC, 0.1% SDS. The filters were dried and exposed to x-ray film overnight at room temperature. Plaques aligning with positive signals from the primary screen were cored and replated at a lower density to allow the isolation of independent positive plaques. The secondary screens were hybridized and washed according to the methods listed above. Six positive plaques were chosen and rescued according to Short, J. M. et al. 1988 *Nucl. Acids Res. Vol* 16: 7583–7600 and 10 µl of the heat-killed phage stock was used to infect fresh XL1-Blue cells. Analysis of the cDNA inserts were performed as described in Example 2. At least three clones contained DNA inserts which were full length as judged by the size of the cDNA insert.

EXAMPLE 4

To demonstrate that cDNA includes internal restriction sites that are contained in the linker/primer can be cloned intact, a cDNA library was constructed with polyadenylated RNA that had been synthesized in vitro.

RNA transcripts were synthesized from 5 µg of a plasmid template pBMG419 which was obtained from Dr. James Boulter of the Salk Institute, La Jolla, Calif. Before transcription the template was cleaved with 20 units of EcoR I (Stratagene, La Jolla, Calif.) at 37° C. for 2 hrs. The plasmid was then transcribed with 60 units of SP6 DNA polymerase (Epicentre) in a reaction volume of 280 µl under conditions described in Melton, D. A., et al., (1984) *NAR* 12: 7035–7056. Full length cDNA clones constructed from this RNA template were expected to contain Xho I restriction sites. Therefore analysis of full length cDNA clones obtained from a library constructed from this RNA can be used to determine that cDNAs containing Xho I restriction sites can be cloned intact with the methods described in the present invention. Such a library was constructed using 2.5 µg of the RNA as described above as a template. The construction of the library was identical as described in Example 1. Synthesis of the cDNA with 5-methyl-dCTP was compared with an identical synthesis with dCTP. This was done to demonstrate that the cDNA was full length and was substantially protected from digestion with Xho I when 5-methyl dCTP was used for synthesis of the first strand cDNA when compared to cDNA synthesized with dCTP. FIG. 3 shows the results of the gel electrophoresis analysis of the products of first and second strand cDNA synthesis and digestion of the double stranded cDNA with Xho I. This data demonstrates that the cDNA synthesized with 5-methyl dCTP was full length and it was substantially protected from digestion with Xho I during its initial cloning. Ten clones that resulted from this construction were excised and analyzed as described in Example 2. Of the ten clones analyzed we determined that 6 contained the expected internal Xho I site. A film of the gel electrophoresis analysis is shown in FIG. 4.

EXAMPLE 5

This example demonstrates the selection of an appropriate combination of nucleotide analogs and restriction endonucleases for the synthesis of cDNA and construction of directional cDNA libraries.

Primer Extension of Single-stranded DNA Using Klenow Fragment and Methylated dCTP 100 nanograms of –20 primer (Stratagene, La Jolla, Calif.) was radioactively labeled with 10 units of Polynucleotide kinase (Stratagene, La Jolla, Calif.) and 600 µCi of gamma $^{32}$P ATP (NEN, Boston Mass.) in the presence of 50 mM Tris-HCl (pH 8.0), 7 mM MgCl$_2$, 1 mM Dithiothreitol at 37° C. for 30 minutes in a total volume of 40 µl. Unincorporated nucleotides were removed from the primer by centrifugation through a Trisacryl GF-05 M (IBF Biotechnics, Villenenve-La Garenne, France) spin column. 20 µl of the labeled primer was annealed to 1 µg of pBluescript KS+ plasmid (Stratagene, La Jolla, Calif.) by heating the two together at 65° C. for ten minutes followed by a 5 minute incubation at room temperature. The primer was extended with either a 0.125 mM dNTP mix, or a 0.125 mM mixture of dATP, dGTP, dTTP and 5-methyl deoxycytosine.

Both reactions occurred in the presence of 50 mM Tris-HCl (pH 8.0), 7 mM MgCl$_2$, 1 mM dithiothreitol and 10 units of Klenow fragment in a total volume of 40 µl. The reactions were incubated at 37° C. for 10 minutes then at room temperature for 30 minutes. The double-stranded DNA was purified by phenol extraction followed by a phenol phase back-extraction with 20 µl of 5T.1E. The hemimethylated DNA and the control DNA were digested with 5 to 10 units of each of the following restriction enzymes in the manufacturer's recommended buffers: Bst XI, Xho I, Xba I, Acc I, Hpa II, Spe I, and Not I. All reactions were carried out with 5 µl of DNA at 37° C. for 2 hours except for Bst XI which was incubated at 65° C. The samples were boiled in the presence of formamide for 5 minutes then run on a 6% denaturing acrylamide gel. The gel was exposed to Kodak XOMAT x-ray film for 12 hours at room temperature. Synthesis of DNA with 5-methyl dCTP substantially protected Hpa II, Acc I, Bst XI, Xho I, Spe I, Not I, and partially protected Xba I sites.

It will be apparent to those skilled in the art that modifications and changes to the above-described embodiments of the invention will be possible without departing from the spirit and scope of the invention. It is intended that the following claims be interpreted to embrace all such modifications and changes.

What is claimed is:

1. A method of synthesizing a double-stranded cDNA having a first strand complementary to an mRNA template, comprising the steps:

synthesizing the first strand by contacting, under conditions effective to permit polymerization of the first strand, the ERNA template with:

(a) a polynucleotide linker/primer defining a first restriction site and being sufficiently complementary to the mRNA template to hybridize therewith;

(b) a reverse transcriptase;

(c) deoxyribonucleotide triphosphate substrates comprising a methylated deoxyribonucleotide triphosphate analog, wherein the linker/primer and the methylated deoxyribonucleotide triphosphate analog are selected such that the linker/primer is capable of being cleaved at the first restriction site and incorporation of the methylated deoxyribonucleotide triphosphate analog into the first strand protects the double-stranded DNA from cleavage under conditions sufficient to cleave the linker/primer at the restriction site, synthesizing a second cDNA strand complementary to said first cDNA strand, whereby a double stranded cDNA is produced, and ligating restriction site adaptors to said double stranded cDNA, wherein said adaptors comprise a second restriction site that is different from the first restriction site.

2. A method according to claim 1, wherein said deoxyribonucleotide triphosphate analog is 5-methyl dCTP.

3. A method according to claim 1, wherein said reverse transcriptase is avian myoblastoid virus reverse transcriptase.

4. The method according to claim 1, wherein said reverse transcriptase is murine moloney leukemia virus reverse transcriptase.

5. A method according to claim 1, wherein the deoxyribonucleotide triphosphate analog is 5-methyl dCTP.

6. A method according to claim 1, wherein only the first strand of the double-stranded DNA comprises methylated nucleotide analogs.

7. A method according to claim 5, wherein the reverse transcriptase is selected from the group consisting of avian myoblastoid virus reverse transcriptase and murine moloney leukemia virus reverse transcriptase.

8. A kit for the synthesis of cDNA, said kit comprising reverse transcriptase and methylated nucleotide analog, and a linker/primer polynucleotide.

9. A kit according to claim 8, wherein said reverse transcriptase is avian myoblastoid virus reverse transcriptase or murine moloney leukemia virus reverse transcriptase.

* * * * *

UNITED STATES PATENT AND TRADEMARK OFFICE
CERTIFICATE OF CORRECTION

PATENT NO. : 5,681,726
DATED : October 28, 1997
INVENTOR(S) : William David Huse and Connie Jo Hansen It is certified that error appears in the above-identified patent and that said Letters Patent is hereby corrected as shown below:

Claim 1, column 16,
Line 37, delete "ERNA" and insert therefor -- mRNA --.

Signed and Sealed this

Eighteenth Day of September, 2001

Attest:

NICHOLAS P. GODICI
Attesting Officer    Acting Director of the United States Patent and Trademark Office